United States Patent [19]

Emmel et al.

[11] 4,216,213
[45] Aug. 5, 1980

[54] ACARICIDAL AND INSECTICIDAL COMPOSITIONS

[75] Inventors: Ludwig Emmel, Frankfurt am Main; Hans Röchling, Bad Soden am Taunus; Günther Seyfarth, Kelkheim, all of Fed. Rep. of Germany

[73] Assignee: Hoechst Aktiengesellschaft, Frankfurt, Fed. Rep. of Germany

[21] Appl. No.: 32,767

[22] Filed: Apr. 24, 1979

[30] Foreign Application Priority Data

Apr. 27, 1978 [DE] Fed. Rep. of Germany ....... 2818497

[51] Int. Cl.$^2$ .......................... A01N 9/36; A01N 9/24
[52] U.S. Cl. ...................................... 424/219; 424/314
[58] Field of Search ................................ 424/314, 219

[56] References Cited

U.S. PATENT DOCUMENTS

| 3,600,474 | 8/1971 | Böhner et al. | 424/219 |
| 3,769,377 | 10/1973 | Selms | 424/219 |

FOREIGN PATENT DOCUMENTS

| 703454 | 4/1966 | Italy | 424/314 |
| 45-2038 | 1/1970 | Japan | 424/314 |

OTHER PUBLICATIONS

The Merck Index, 9th Ed., Item 3283, (1976).

*Primary Examiner*—Douglas W. Robinson
*Attorney, Agent, or Firm*—Curtis, Morris & Safford

[57] ABSTRACT

Acaricidal and insecticidal compositions containing as active ingredient a combination of (7-chloro-bicyclo[3,2,0]-hepta-2,6-dien-6-yl)dimethyl phosphate (I) with 2-sec.butyl-4,6-dinitrophenyl-3-methyl crotonate (II) or with 2-sec.butyl-4,6-dinitrophenyl-isopropyl carbonate (III) in a proportion by weight of compounds I:II or I:III in the range of from 1:20 to 20:1 have a synergistic effect against acaridae and their eggs and simultaneously against insects.

3 Claims, No Drawings

ACARICIDAL AND INSECTICIDAL COMPOSITIONS

It is known that spider mites and plant lice are important pests in horticulture, vegetable culture and crop farming. They occur in the open field as well as under glass and considetably impair the quality and reduce the quantity of the crop plants by their sucking and, as regards plant lice, by acting as vectors for phytopatogenous viruses.

Plant lice and spider mites often occur simultaneously as pests in crops and, therefore, it is desirable to combat them simultaneously, that is to say in one operation.

Heptenosphos [(7chloro-bicyclo[3,2,0]hepta-2,6-dien-6-yl)dimethyl phosphate] is known to be a very effective insecticide (cf. H. Martin, "Pesticide Manual", 5th edition 1977, page 295); Binapacryl [2-sec.butyl-4,6-dinitrophenyl-3-methyl crotonate] and Dinobuton [2-sec.-butyl-4,6-dinitro-phenyl isopropyl carbonate] are both very effective acaricides (cf. loc. cit. pages 42 and 208).

When testing combinations of the aforesaid substances, it has been found surprisingly that mixtures of Heptenophos with Binapacryl or with Dinobuton exhibit synergistic effects in acaricidae as well as in insects, that is to say by adding Dinobuton or Binapacryl to Heptenophos (little effective as insecticide in itself) the insecticidal effect of the latter can be considerably improved and, vice versa, by adding Heptenophos having a minor effect only against spider mites to Dinobuton or Binapacryl, the acaricidal effect of the two latter compounds can be greatly improved.

It is, therefore, the object of the present invention to provide pesticidal compositions containing as active ingredients (7-chloro-bicyclo[3,2,0]-hepta-2,6-dien-6-yl)dimethyl phosphate (I) in combination with 2-sec.butyl-4,6-dinitrophenyl-3-methyl crotonate (II) or with 2-sec.butyl-4,6-dinitro-phenyl-isopropyl carbonate (III). The proportion by weight of the active compounds I:II or I:III can vary within wide limits, for example in the range of from 1:20 to 20:1.

The pesticidal compositions according to the invention exhibit an outstanding effect against noxious insects and acaricidae and their eggs and they can be used with success in much smaller amounts and concentrations than pesticides containing only one of the two active ingredients. Moreover, the compositions of the invention are effective against strains of acaridae that are resistant to phosphoric acid esters.

They can also be used with success to combat other noxious arthropods such as fruit flies, bugs, ants and mealybugs. The compositions are well tolerated by numerous crop plants. There are mentioned, for example, lettuce, tomato, parsley, borage, a great number of roses, dieffenbachia, carnations, peas, potato, dwarf beans, horse beans and others.

The mixtures of active substances according to the invention can be used in the form of the usual formulations such as emulsion concentrates, ULV solutions, wettable powders, dusts, sprays or granules.

Emulsifiable concentrates are obtained by dissolving the active compounds in suitable organic solvents with the addition of non ionic, surface active agents as emulsifier, for example a polyoxethylated alkyl phenol, a polyoxethylated triglyceride or fatty alcohol or a polyoxethylated oleyl or stearyl amine. Suitable solvents are, for example, toluene, xylenes, chlorbenzenes and other aromatic compounds of high boiling point; gasolines or paraffin oils, cyclohexanone, dimethyl formamide, dimethyl sulfoxide, tetrahydrofurane, dioxane, diacetone alcohol, ethyl acetate and isophorone.

In the case of "Ultra-Low-Volume" (ULV) formulations high boiling solvents are suitably used in order to keep low the rate of evaporation during spraying, for example high boiling paraffins, ketones or esters and optionally vegetable oils.

Suitable carrier materials for solid formulations are, above all, mineral substances, for example silicic acids and silicates, such as kieselguhr, kaolins, alumina or talcum, chalk or siliceous chalks, as well as preparations of the said mineral substances with auxiliaries such as stearates, alkyl, aryl or alkylaryl sulfonates, lignosulfonates and the like. Formulations for specific applications may contain further wetting agents, dispersing agents and adhesives as well as grinding auxiliaries of the most different types.

Commercial formulations according to the invention have a total content of active ingredients in the range of from about 10 to 90% by weight. They further contain the usual adhesives, wetting agents, dispersing agent, emulsifiers, penetration auxiliaries, solvents, fillers and carriers. For practical use, tank mixtures containing the individual active ingredients in an appropriate mixing proportion can also be used.

Prior to application, the emulsion concentrates, wettable powders or dispersions are further diluted with a suitable diluant, usually water, to the concentration suitable for practical application. The concentration varies as usual, depending on the type of application and climatic conditions, especially temperature and moisture. With wettable powders, for example, it is generally in the range of from 0.005 to 1.0% by weight of total amount of active compounds.

The following examples illustrate the invention.

EXAMPLES OF FORMULATION (1) Emulsion concentrate (proportion by weight of Heptenophos to Binapacryl or Dinobuton=1:1)

| | |
|---|---|
| Heptenophos | 25 |
| Binapacryl or Dinobuton | 25 |
| castor oil polyglycol ether (40 EO) | 6.4 |
| triisobutylphenol polyglycol ether (50 EO) | 1.6 |
| xylene | 42.0 |
| | 100. % b. w. |

(2) Emulsion concentrate (proportion by weight of Heptenophos to Binapacryl or Dinobuton=1:4)

| | |
|---|---|
| Heptenophos | 10 |
| Dinobuton or Binapacryl | 40 |
| castor oil polyglycol ether (50 EO) | 6.4 |
| triisobutylphenol polyglycol ether (50 EO) | 1.6 |
| xylene | 42.0 |
| | 100. % b. w. |

(3) Emulsion concentrate (proportion by weight of Heptenophos to Binapacryl or Dinobuton=1:10)

| | |
|---|---|
| Heptenophos | 4.5 |
| Binapacryl or Dinobuton | 45.5 |
| castor oil polyglycol ether (40 EO) | 6.4 |
| triisobutylphenol polyglykol ether (50 EO) | 1.6 |
| xylene | 42.0 |

-continued

|   |   |   |
|---|---|---|
|   | 100. | % b. w. |

(4) Spray formulation (proportion by weight of Heptenophos to Binapacryl or Dinobuton about 1:1)

|   |   |
|---|---|
| Heptenophos | 0.0526 |
| Binapacryl | 0.051 |
| methylene chloride | 59.8964 |
| propellant | 40.0 |
|   | 100.0000 b. w. |

(5) Spray formulation (proportion by weight of Heptenophos to Binapacryl 2:1)

|   |   |
|---|---|
| Heptenophos | 0.0526 |
| Binapacryl | 0.0253 |
| methylene chloride | 59.9221 |
| propellant | 40.0000 |
|   | 100.0000 b. w. |

BIOLOGICAL EXAMPLES

The mixtures and, for comparison, the individual components alone were emulsified or suspended in water in amounts such that the concentrations of active ingredients indicated in Tables 1, 2, and 3 were obtained in percent by weight.

Plants infested with full populations of the pests were sprayed with the spray liquors obtained until all parts were covered. After drying of the layer containing the active ingredient, the plants were placed in the greenhouse at 20° C.

The results were evaluated 8 and 3 days, respectively, after the treatment. The values found are indicated in the tables.

Table 1

| Combated pests: spider mites (*Tetranychus urticae*) in beans (*Phaseolus vulgaris*) | | |
|---|---|---|
| active substance AS | % by weight of AS in spray liquor | acaricidal/ovicidal effect after 8 days % of destruction |
| I Heptenophos | 0.06 | % 0 |
| II Binapacryl | 0.006 | 86 85 |
|   | 0.003 | 65 40 |
| I Heptenophos + II Binapacryl (10:1) | 0.06 + 0.006 | 100 98 |
| I Heptenophos + II Binapacryl (20:1) | 0.06 + 0.003 | 90 85 |

Table 2

| Combated pests: spider mites (*Tetranychus urticae*) in beans (*Phaseolus vulgaris*) | | |
|---|---|---|
| active substance AS | % by weight of AS in spray liquor | acaricidal/ovicidal effect after 8 days % of destruction |
| I Heptenophos | 0.06 | 4 0 |
| III Dinobuton | 0.006 | 82 76 |
|   | 0.003 | 52 35 |
| I + III (10:1) | 0.06 + 0.006 | 97 89 |
| I + III (20:1) | 0.06 + 0.003 | 85 62 |

Table 3

| Combated pest: bean aphid (*Doralis fabae*) in horse beans (*Vica faba*) | | |
|---|---|---|
| active substance AS | % by weight of AS in spray liquor | % of destruction after 3 days |
| I Heptenophos | 0.0002 | 47 |
| II Binapacryl | 0.002 | 18 |
|   | 0.001 | 5 |
| I + II (1:10) | 0.0002 + 0.002 | 92 |
| I + II (1:5) | 0.0002 + 0.001 | 73 |

What is claimed is:

1. An acaricidal and insecticidal composition consisting essentially of a mixture of (7-chloro-bicyclo-[3,2,0]hepta-2,6-dien-6-yl)dimethyl phosphate (compound I) with 2-sec.butyl-4,6-dinitrophenyl-3-methyl crotonate (compound II) or with 2-sec.butyl 4,6-dinitrophenyl-isopropyl carbonate (compound III), the weight ratio of compound I to compound II or to compound III being from 1:20 to 20:1.

2. A method of combating pests selected from acaridae and insects which comprises applying to soils, substrates, objects or living beings infested with said pests an acaricidally or insecticidally effective amount of the composition as claimed in claim 1.

3. An acaricidal and insecticidal composition comprising an inert carrier and an acaricidally or insecticidally effective amount of a mixture of (7-chloro-bicyclo-[3,2,0]hepta-2,6-dien-6-yl)dimethyl phosphate (compound I) with 2-sec.butyl-4,6-dinitrophenyl-3-methyl crotonate (compound II) or with 2-sec.butyl 4,6-dinitrophenyl-isopropyl carbonate (compound III), the weight ratio of compound I to compound II or to compound III being from 1:20 to 20:1.

* * * * *